United States Patent [19]

Ross et al.

[11] Patent Number: 4,786,593
[45] Date of Patent: Nov. 22, 1988

[54] DIAGNOSTIC METHOD FOR DETECTION OF NEURAL CREST DISEASE

[75] Inventors: Alonzo Ross, Bensalem; Hilary Koprowski; Meenhard Herlyn, both of Wynnewood, all of Pa.

[73] Assignee: Wistar Institute of Anatomy and Biology, Philadelphia, Pa.

[21] Appl. No.: 723,760

[22] Filed: Apr. 16, 1985

[51] Int. Cl.$^4$ .................. G01N 33/53; G01N 33/567; G01N 33/543

[52] U.S. Cl. .......................... 435/7; 436/503; 436/504; 436/518; 436/548; 436/813; 436/817; 935/110

[58] Field of Search ............... 436/811, 813, 518, 504, 436/817, 503, 514, 515, 543, 547, 548, 64, 804; 435/68, 7; 935/106, 108, 110

[56] References Cited

U.S. PATENT DOCUMENTS

4,444,744 4/1984 Goldenberg ..................... 424/1.1
4,562,160 12/1985 Real et al. ......................... 436/813

OTHER PUBLICATIONS

Green and Greene, J. Biol. Chem., 1986, vol. 261, pp. 15316–15326.
Johnson et al, Cell, 1986, vol. 47, pp. 545–554.
Radeke et al, Nature, 1987, vol. 325, pp. 593–597.
Herlyn et al, "Production and Characterization of Monoclonal Antibodies Against Human Malignant Melanoma," Cancer Investigation 1(3), 215–224 (1983).
Revoltella et al, "Specific Binding of Nerve Growth Factor (NGF) by Murine C 1300 Neuroblastoma Cells," J. Exp. Med., 140, (1974).
Fabricant et al, "Nerve Growth Factor Receptors On Human Melanoma Cells in Culture," Proc. Natl. Acad. Sci. USA, vol. 74, No. 2, 565–569 (1977).
Chandler et al, "A Monoclonal Antibody Modulates the Interaction of Nerve Growth Factor with PC12 Cells," J. Biol. Chem. vol. 259, No. 11, 6882–6889 (1984).
Schechter et al, "Nerve Growth Factor Receptors On PC12 Cells: Evidence for Two Receptor Classes with Differing Cytoskeletal Association," Cell, vol. 24, 867–874 (1981).
Massague et al, "Identification of a Nerve Growth Factor Receptor Protein in Sympathetic Ganglia Membranes by Affinity Labelling," J. Biol. Chem. vol. 256, No. 18, 9419–9424 (1981).
Vale et al, "Alteration of Binding Properties and Cytoskeletal Attachment of Nerve Growth Factor Receptors in PC12 Cells by Wheat Germ Agglutinin," J. Cell Biol., vol. 94, 710–717 (1982).
Grob et al, "Affinity Labeling and Partial Purification of Nerve Growth Factor Receptors from Rat Pheochromocytoma and Human Melanoma Cells," Proc. Natl. Acad. Sci. USA, vol. 80, 6819–6823 (1983).
Buxser et al, "Change in State of Nerve Growth Factor Receptor," J. Biol. Chem., vol. 258, No. 6, 3741–3749 (1983).
Sherwin et al, "Human Melanoma Cells Have Both Nerve Growth Factor and Nerve Growth Factor-Specific Receptors on Their Cell Surfaces," Proc. Natl. Acad. Sci., USA vol. 76, No. 3, 1288–1292 (1979).
Landreth et al, "Nerve Growth Factor Receptors on PC12 Cells: Ligand-Induced Conversion from Low-To-High-Affinity States," Proc. Natl. Acad. Sci., USA, vol. 77, No. 8, 4751–4755 (1980).
Block et al, "The Nerve Growth Factor Receptor On PC12 Cells: Interconversion Between Two Forms with Different Binding Properties," J. Neurochem., vol. 40, No. 6, 1654–1663 (1983).
Puma et al, "Purification of the Receptor for Nerve Growth Factor from A875 Melanoma Cells by Affinity Chromatography," J. Biol. Chem., vol. 25i, No. 5, 3370–3375 (1983).
Ross et al, "Characterization of Nerve Growth Factor Receptor in Neural Crest Tumors Using Monoclonal Antibodies," Proc. Natl. Acad. Sci. USA 81, 6681–6685 (1984).
Buxser et al, "Properties of the Nerve Growth Factor Receptor," J. Biol. Chem., vol. 260, No. 3, 1917–1926 (1985).
Grob et al, "Characterization of the Human Melanoma Nerve Growth Factor Receptor," J. Biol. Chem., vol. 260, No. 13, 8044–8049 (1985).
Breakefield et al, "Structural Gene for $\beta$-Nerve Growth Factor Not Defective in Familial Dysautonomia," Proc. Natl. Acad. Sci. USA 81, 4213–4216 (1984).
Chemical Abstracts, vol. 102, p. 471, Abstract No. 164995d, Morgan and Bradshaw, 1985.
American Type Culture Collection Catalogue, p. 290, 1985.

*Primary Examiner*—Robert J. Warden
*Assistant Examiner*—Florina B. Hoffer
*Attorney, Agent, or Firm*—Banner, Birch, McKie and Beckett

[57] ABSTRACT

It has been determined that nerve growth factor binds to a cell surface protein of human neural crest origin having a molecular weight of about 75,000 daltons. New monoclonal antibodies specifically imunoprecipitate these receptor molecules, and also inhibit binding of the hormone to the receptor. These monoclonal antibodies show significantly higher reactivity with primary and metastatic melanoma cell lines than with melanocytes. The antibodies are used in a diagnostic method for histochemical detection of human neural crest disease.

13 Claims, No Drawings

DIAGNOSTIC METHOD FOR DETECTION OF NEURAL CREST DISEASE

BACKGROUND OF THE INVENTION

Nerve growth factor (NGF) regulates the development of sympathetic and sensory neurons and other cell types derived from the neural crest. Like other peptide hormones, NGF must physically interact with the cell surface in order to exert its influence on cell development. This surface interaction is mediated by a glycoprotein called nerve growth factor receptor which specifically binds the hormone. A full understanding of subsequent steps is lacking, although there is a variety of speculation in the literature. For example, after binding NGF, the receptor might change its physical properties or its cellular location or might even acquire hormone-dependent enzymatic activity.

Derangement of the development of the neural crest leads to a number of disorders of clinical interest. One derangement of neural crest tissue leads to tumors such as melanomas. Many melanoma cell lines have been shown to bind significantly more NGF than either normal cells or other tumor cells [PNAS 74, 565–569 (1977)]. Genetic methods of identifying the cause of the malignancy, however, have been inconclusive (*Nature* Vol. 308, pp. 69–62, 1984).

There is a need for a ready diagnostic method to identify when derangement of development of neural crest has occurred.

SUMMARY OF THE INVENTION

It is an object of this invention to provide a diagnostic method for detection of the human neural crest cancers such as melanoma.

It is another object of this invention to provide a diagnostic method for identification of the human cancer melanoma employing antibodies specific for human NGF receptors.

It is an additional object of this invention to provide antibodies with reactivity directed specifically to human NGF receptors.

It is a further object of this invention to provide hybrid cell lines which produce monoclonal antibodies with reactivity directed specifically to human NGF receptors.

It is yet another object of this invention to provide antibodies which will immunoprecipitate human NGF receptors.

In accordance with this invention, there is provided, a diagnostic method for histochemical detection of the human neural crest cancers such as melanomas in which humans cells are contacted with a monoclonal antibody specific for NGF receptors having an apparent molecular weight of about 75,000 daltons, and determining the concentration of NGF respectors in the cytoplasm and at the cell surface. In one of its aspects, the invention embraces anti-NGF receptor antibodies, and in another of its aspects the invention is directed to a hybridoma cell line which produces anti-NGF receptor antibodies.

It has been discovered by the present inventors that melanoma cells have significantly more NGF receptors which can be bound by antibody than do normal melanocytes; this implicates the receptors in the etiology of the malignancy. Accordingly, this invention permits a quick and effective means for the diagnosis of melanoma.

This invention provides an antibody directed against human NGF receptor which inhibits hormone (NGF) binding. It is capable of immunoprecipitating its cognate antigen (NFG receptor), and that antigen is the low affinity (or fast $K_D$) variety of NGF receptor, having apparent molecular weight of 75,000 daltons.

DETAILED SUMMARY OF THE INVENTION

The general method used for production of antibody-secreting somatic cell hybrids has been previously described, inter alia, in *Proceedings of National Academy of Sciences USA*, Vol. 75, pp. 3405–3409 (1978) and in Koprowski U.S. Pat. No. 4,172,124 entitled "Method of Producing Tumor Antibodies." Methods for obtaining hybridomas are, of course, quite well known in the art.

The hybridoma cells can be grown in culture to produce the antibodies of this invention, which are secreted into the medium. Any of a variety of known media can be employed for the culture of hybridomas and the recovery of antibodies, and the choice is easily within the skill of the art. One particularly satisfactory medium is Dulbecco's minimal essential medium (MEM) containing approximately 20% fetal calf serum. Preferably, the medium chosen will be substantially free of antibodies so that subsequent purification steps to remove those unwanted antibodies can be avoided.

Since it has now been determined in accordance with this invention that an antibody is desirable which is specific for the approximately 75,000 dalton protein which binds nerve growth factor, corresponding antibodies can be made by challenging other animals with melanoma cells and also by employing hybrid cells obtained from animals other than mice. For example, mouse, rat, or human cells can be used, as can any combination of cells so long as the cells of one species fuse with the other.

The antibodies employed for the diagnostic methods of this invention, are those which are specific for the NGF receptor that has a molecular weight of about 75,000. The receptor is a glycoprotein that has a dissociation constant ($K_D$ of about $2 \times 10^{-9}$M). Such receptor is recognized by the antibody produced by the hybridoma deposited with the American Type Culture Collection, Rockville, MD as accession No. HB-8732, deposited Mar. 1, 1985.

This invention contemplates the use of any antibody that recognizes the NGF receptor having a molecular weight of about 75,000. Preferred antibodies for the practice of this invention are those that correspond to the antibody produced by the cell line deposited with the American Type Culture Collection, accession No. HB-8737. "Correspond to" means antibodies which recognize the same antigen as those produced by American Type Culture Collection accession No. HB-8737. Such correspondence can readily be determined by employing known blocking tests. Such tests establish whether the binding of the antibody produced by deposit No. HB-8737 to the protein is reduced by first contacting the protein with the candidate antibody. The antibodies useful in this invention include all isotypes.

Cells to be contacted with the antibody of the present invention can be fixed, or fresh tissue. Such choice of cell state and medium in which antibody-cell incubation is to be conducted is well within the skill of the art.

Determining the concentration of NGF receptors in human cells can be accomplished by any of a variety of techiniques well known in the art. For example, radioimmunoassay, immunofluorescence, immunoassay employing a coupled enzyme which generates a colored product, can all be employed to quantitate antibody binding to cells.

EXAMPLE I

Briefly, a BALB/c mouse was immunized with $4 \times 10^6$ WM 245 melanoma cells (Cancer Research 40, 3602–3609, 1980,) or WM 115 cells three days before sacrifice. Spleen cells from this mouse were fused with myeloma cells of cell line P3×63Ag8 in the presence of polyethylene glycol. Hybrids were selected in HAT selective medium. Fused cells were seeded in wells of tissue culture plates. Twenty days post-fusion, single colonies were picked and cloned.

To identify the antibodies of this invention, relative binding to two melanoma cell lines was examined using radioimmunoassays. The two lines, SK MEL 37 (gift of Dr. K. O. Lloyd of the Sloan Kettering Institute) and A875 (gift of Dr. G. J. Todaro of the National Institutes of Health), are known to bind different amounts of NGF; the latter binding more than the former. Antibodies were selected which bound in greater amounts to A875 cells than to SK MEL 37 cells.

EXAMPLE II

The antibodies of the present invention were found to inhibit the binding of $[^{125}I]NGF$ to A875 melanoma cells. The cells and hybridoma supernatants containing antibodies were incubated together at 37° C. for 30 minutes, after which 100,000 cpm of $[^{125}I]NGF$ were added. This mixture was incubated for a further 30 minutes at 37° C., after which the mixture was pelleted through 10% sucrose. The cells formed a pellet, whereas unbound $[^{125}I]NGF$ remained in the supernatant. The pellet was counted in a gamma counter to determine the amount of radioactive NGF bound to the cells. Non-saturable binding was measured in the presence of 10 ug/ml unlabeled NGF and subtracted. In the presence of the supernatants containing the antibodies of the present invention, $[^{125}I]NGF$ binding to A875 cells was reduced by 78–93%. 100% binding was determined in the presence of non-specific supernatant of the myeloma cells P3×63Ag8.

Purified antibodies were used in a similar manner to inhibit $[^{125}I]$-NGF binding, but the concentration of antibodies was varied over a range of zero to 1,500 ng/ml IgG. The inhibition caused by antibodies of the present invention was found to be dose dependent, requiring between 300 ng/ml and 700 ng/ml for 50% inhibition.

EXAMPLE III

The binding of $[^{125}I]$-labelled antibody of the present invention and of $[^{125}I]$-NGF to A875 melanoma cells was quantitated independently. Scatchard analysis (1949, *Annals of the New York Academy of Science*, Vol. 51, pp. 660–672) of the data indicated that NGF binds to its receptor on A875 cells with a $K_D$ of approximately $2 \times 10^{-9}$M. The analysis also indicated that the numbers of binding sites per cell were roughly equivalent, there being $8 \times 10^5$ sites for the antibody and $1 \times 10^6$ sites for the hormone. This is consistent with the premise that they both are binding the same component, NGF receptor. The results of the following example confirm that premise.

EXAMPLE IV $[^{125}I]$-NGF was bound to A875 cells. To covalently join the NGF to the cells, the cross-linking agent, ethyldimethylisopropylaminocarbodiimide was added, and the cells were subsequently solubilized with detergent. The solubilized cells, containing $[^{125}I]$-NGF cross-linked to its receptor, were then incubated with hybridoma supernatant of this invention and of the control supernate P3×63Ag8. Immunoprecipitated products were separated by SDS-polyacrylamide gel electrophoresis, and detected by autoradiography. The supernatant of the hybridoma of this invention immunoprecipitated a diffuse-banding product of approximately 90,000 daltons.

Since that product was cross-linked to $[^{125}I]$-NGF, it was expected that the molecular weight of one NGF monomer (13,000 daltons) would have to be subtracted to obtain a correct estimate of the molecular weight of the NGF receptor itself. This expectation was verified by immunoprecipitation of detergent solubilized A875 cells which had been grown in the presence of $[^{35}S]$-cysteine. The product of this precipitation was subsequently subjected to SDS-polyacrylamide electrophoretic separation and was found to have an apparent molecular weight of approximately 75,000 daltons. The diffuse banding is due to heterogeneous glycosylation. That is approximately 75,000 dalton protein is, in fact, glycosylated was shown by metabolically labelling it with [3H]-glucosamine, and by inhibition of the glycosylation with the drug tunicamycin.

EXAMPLE V

Monoclonal antibody of this invention was used as a histochemical reagent for both frozen and fixed tissues. This was accomplished by first allowing the monoclonal antibodies to bind to the tissue sections, and then binding those antibodies with biotinylated anti-mouse antibody (Vector Laboratories, Burlingame, Calif.). Successive reagent additions were performed of avidin: biotinylated peroxidase complex (vector Laboratories) and aminoethylcarbazole with hydrogen peroxide, thus staining the sections red. They were counter-stained with hematoxylin. Alternative fixing, staining and counter-staining methods will be apparent to those skilled in the art. Results of this staining procedure are seen in Table 1.

TABLE 1

Immunoperoxidase staining with anti-NGF receptor antibody of frozen and fixed tissue sections.

| Tissue | Fixation | Ratio of positive samples to samples examined | Site of staining |
| --- | --- | --- | --- |
| Melanocytes | frozen | 0/11 | — |
| Nevi | frozen | 5/5 | Cytoplasmic |
| Melanomas | frozen | 6/9 | Cytoplasmic |
| A875 melanoma cell line | frozen | 1/1 | Plasma membrane |
|  | fixed | 1/1 | Plasma membrane |
| Peripheral nerves | frozen | 8/8 | Neural sheath |
|  | fixed | 5/5 | Neural sheath |
| Neurofibromas | fixed | 2/4 | Cytoplasmic |
| Pheochromocytomas | frozen | 1/1 | Cytoplasmic |
| Pancreas* | frozen | 0/1 | — |
| Adrenal gland | fixed | 0/1 | — |

*Autopsy tissue, 5 hr postmortem.

There was no staining evident of normal melanocytes, whereas, primary and metastatic melanomas, neurofibromas, pheochromocytomas, and dysplastic or common nevi all were stained diffusely throughout the cytoplasm and/or cell membranes. The melanoma cell line, A875, showed a strong staining pattern, particularly localized at the plasma membrane. Tissues such as pancreas and adrenal gland did not stain with this antibody staining technique.

The monoclonal antibodies of this invention will be used to target anti-tumor agents. This will be done by making conjugates of the antibodies to toxins and administering those conjugates directly to tumor-bearing patients. This targeting will reduce the generalized deleterious side effects of chemotherapeutic drugs.

Abundant NGF-receptors on the cell surface of melanomas, relative to normal melanocytes, implicates the hormone itself in transformation and/or metastatic growth. Therefore, the products of this invention, the antibodies to NGF receptors, will be administered to human patients to inhibit the binding of NGF to the receptors. This will impede the cancerous growth.

As shown in the examples above, the antibodies of this invention are functional as a specific histochemical staining reagent. It is anticipated that this will be of great utility in (1) early diagnosis of human melanomas and other neural crest tumors (2) in differential diagnosis of metastases of the lymph nodes to determin the proper therapeutic regimen and prognosis and (3) in the detection and treatment of the genetic diseases neurofibromatosis and familial dysautonomia, where the cause of the disease is thought to be a perturbation of the NGF response.

We claim:

1. A method for the identification of human tumors of neural crest origin which comprises:
    isolating a tissue section from a human, said tissue section comprising human cells;
    contacting said tissue section with an antibody specific for human NGF-receptors having an apparent molecular weight of about 75,000 daltons by SDS-polyacrylamide gel electrophoresis, and determining the concentration of said antibody bound to said cells in the cytoplasm and at the cell surface.

2. The method of claim 1 wherein the human tumor is melanoma.

3. The method of claim 1 wherein the step of contacting said tissue section with an antibody is performed after the cells have been fixed to a slide.

4. The method of claim 1 wherein the step of contacting said tissue section with an antibody is performed after the cells have been frozen.

5. The method of claim 1 wherein the step of contacting said tissue section with an antibody is performed after the cells have been mounted on a slide.

6. The method of claim 1 wherein the step of contacting said tissue section with an antibody is performed after the cells have been solubilized.

7. The method of claim 1 wherein the human tumor is selected from the group consisting of: nevi, melanomas, neurofibromas, and pheochromocytomas.

8. The method of claim 2 wherein the concentration of said antibody determined is compared to the amount found in a control sample comprising normal melanocytes.

9. The method of claim 1 wherein the concentration of said antibody is determined over the course of a therapeutic regimen to monitor the effect of said regimen.

10. The method of claim 1 wherein the antibody is a monoclonal antibody which specifically reacts with human nerve growth factor receptors having a dissociation constant ($K_D$) for its ligand (NGF) of about $2 \times 10^{-9}$M.

11. The method of claim 1 wherein the antibody is produced by a hybridoma deposited at the American Type Culture Collection under Accession No. HB-8737.

12. The method of claim 1 wherein the antibody binds to the same antigen as does the antibody produced by a hybridoma deposited at the American Type Culture Collection under Accession No. HB-8737.

13. The method of claim 1 wherein the determination of the concentration of said antibody is accomplished by a technique selected from the group consisting of: radioimmunoassay, immunofluorescence, and enzyme linked immunoassay.

* * * * *